US010647645B2

(12) United States Patent
Jungong et al.

(10) Patent No.: US 10,647,645 B2
(45) Date of Patent: May 12, 2020

(54) AZEOTROPE OR AZEOTROPE-LIKE COMPOSITIONS OF TRIFLUOROIODOMETHANE (CF3I) AND 1,1,3,3,3,-PENTAFLUOROPROPENE (HFO-1225ZC)

(71) Applicant: Honeywell International Inc., Morris Plains, NJ (US)

(72) Inventors: Christian Jungong, Depew, NY (US); Daniel C. Merkel, Orchard Park, NY (US); Haiyou Wang, Amherst, NY (US); Hang T. Pham, Amherst, NY (US); Ryan J. Hulse, Getzville, NY (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 16/571,921

(22) Filed: Sep. 16, 2019

(65) Prior Publication Data

US 2020/0115304 A1 Apr. 16, 2020

Related U.S. Application Data

(60) Provisional application No. 62/745,657, filed on Oct. 15, 2018.

(51) Int. Cl.

| | |
|---|---|
| ***C07C 21/18*** | (2006.01) |
| ***C07C 19/16*** | (2006.01) |
| ***C07C 17/386*** | (2006.01) |

(52) U.S. Cl.
CPC ............ *C07C 21/18* (2013.01); *C07C 17/386* (2013.01); *C07C 19/16* (2013.01)

(58) Field of Classification Search
None
See application file for complete search history.

(56) References Cited

U.S. PATENT DOCUMENTS

| | | | |
|---|---|---|---|
| 5,444,102 | A | 8/1995 | Nimitz et al. |
| 8,017,030 | B2 | 9/2011 | Singh et al. |
| 8,598,107 | B2 | 12/2013 | Singh et al. |
| 2005/0233923 | A1 | 10/2005 | Singh et al. |
| 2005/0233933 | A1 | 10/2005 | Singh et al. |

FOREIGN PATENT DOCUMENTS

| | | | |
|---|---|---|---|
| EP | 2336266 | B1 | 6/2011 |
| JP | 2000178543 | A | 6/2000 |
| KR | 20000075201 | A | 12/2000 |

*Primary Examiner* — Medhanit W Bahta
(74) *Attorney, Agent, or Firm* — Faegre Drinker Biddle & Reath

(57) ABSTRACT

The present disclosure provides azeotrope or azeotrope-like compositions including trifluoroiodomethane ($CF_3I$) and 1,1,3,3,3-pentafluoropropene (HFO-1225zc), and a method of forming an azeotrope or azeotrope-like composition comprising the step of combining 1,1,3,3,3-pentafluoropropene (HFO-1225zc) and trifluoroiodomethane ($CF_3I$) to form an azeotrope or azeotrope-like comprising 1,1,3,3,3-pentafluoropropene (HFO-1225zc) and trifluoroiodomethane ($CF_3I$) having a boiling point of about −25.63° C.±0.30° C. at a pressure of about 14.44 psia±0.30 psia.

20 Claims, 1 Drawing Sheet

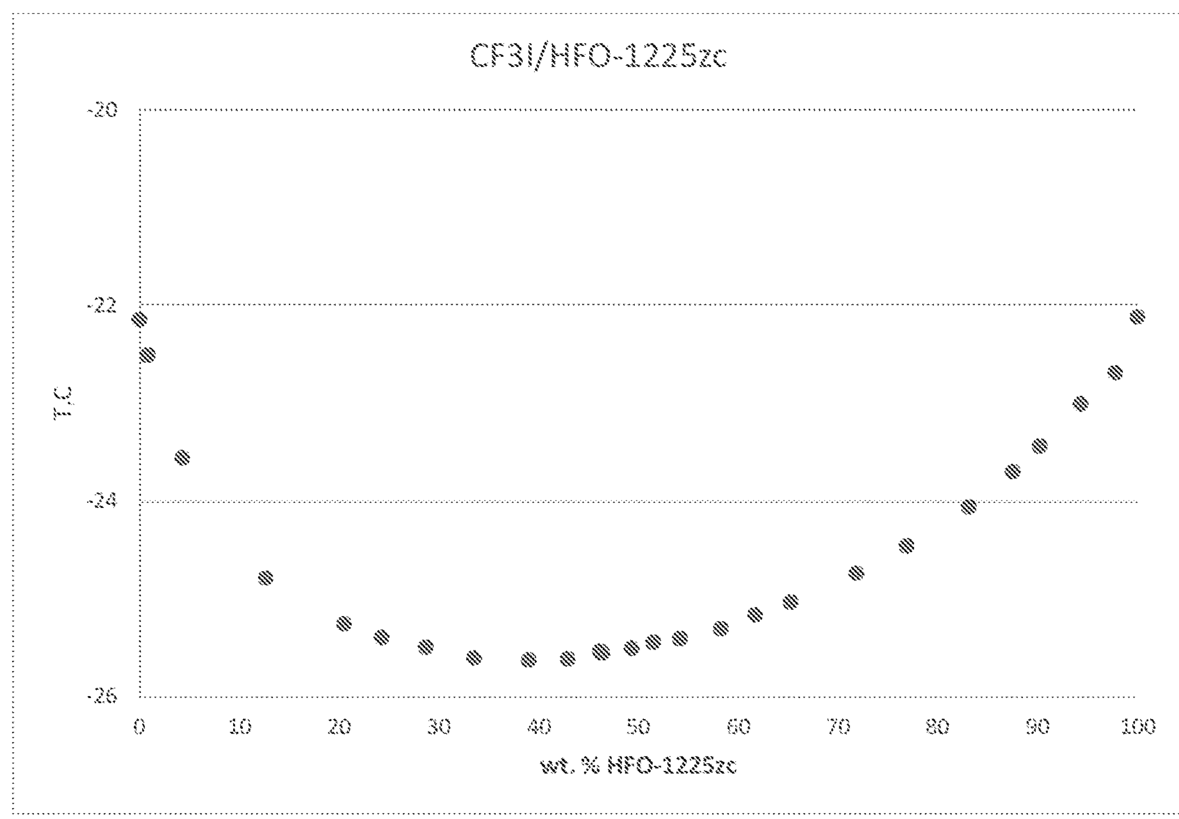
CF3I/HFO-1225zc
-20
-22
-24
-26
T,C
0
10
20
30
40
50
60
70
80
90
100
wt. % HFO-1225zc

AZEOTROPE OR AZEOTROPE-LIKE COMPOSITIONS OF TRIFLUOROIODOMETHANE (CF3I) AND 1,1,3,3,3,-PENTAFLUOROPROPENE (HFO-1225ZC)

CROSS-REFERENCE TO RELATED APPLICATION

This application claims priority to U.S. Provisional Application No. 62/745,657, filed Oct. 15, 2018, which is herein incorporated by reference in its entirety.

FIELD

The present disclosure is related to azeotrope or azeotrope-like compositions and, in particular, to azeotrope or azeotrope-like compositions comprising trifluoroiodomethane ($CF_3I$) and 1,1,3,3,3-pentafluoropropene (HFO-1225zc).

BACKGROUND

Fluorocarbon based fluids have found widespread use in industry in a number of applications, including as refrigerants, aerosol propellants, blowing agents, heat transfer media, gaseous dielectrics, and fire suppression.

However, certain compounds such as chlorofluorocarbons (CFCs) and hydrochlorofluorocarbons (HCFCs) are suspected of depleting atmospheric ozone and, thus, are harmful to the environment. Moreover, some of these compounds are believed to contribute to global warming. Accordingly, it is desirable to use fluorocarbon fluids having low or even zero ozone depletion potential, such as hydrofluorocarbons (HFCs), or those with a photolyzable carbon iodine bond, which exhibit short atmospheric lifetime when released at ground level. The use of single component fluids or azeotrope mixtures, which do not fractionate on boiling and evaporation, is also desirable.

Unfortunately, the identification of new, environmentally-safe, non-fractionating mixtures is complicated due to the fact that azeotrope formation is not readily predictable.

The industry is continually seeking new fluorocarbon-based mixtures that offer alternatives, and are considered environmentally safer substitutes for CFCs, HCFCs and HFCs in use today. Of particular interest are iodide containing compounds and other fluorinated compounds, which have low ozone depletion potentials and low global warming potentials. Such mixtures are the subject of this disclosure.

Although iodide containing compounds are of great potential interest, the purification of iodide containing compounds such as trifluoroiodomethane ($CF_3I$) has presented challenges, and techniques for the removal of impurities from trifluoroiodomethane ($CF_3I$) such as, for example, trifluoromethane (HFC-23), are in constant demand. Therefore, separation techniques such as azeotropic distillation, for example, would be highly desirable.

What is needed are compositions and techniques that may be used to prepare iodide containing compounds, such as trifluoroiodomethane ($CF_3I$), of high purity.

SUMMARY

The present disclosure provides azeotrope or azeotrope-like compositions comprising trifluoroiodomethane ($CF_3I$) and 1,1,3,3,3-pentafluoropropene (HFO-1225zc).

It is well-recognized in the art that it is not possible to predict the formation of azeotropes, and the present inventors have discovered unexpectedly that trifluoroiodomethane ($CF_3I$) and 1,1,3,3,3-pentafluoropropene (HFO-1225zc) form azeotrope or azeotrope-like compositions.

The present disclosure provides a composition comprising an azeotrope or azeotrope-like composition comprising, consisting essentially of, or consisting of, effective amounts of 1,1,3,3,3-pentafluoropropene (HFO-1225zc) and trifluoroiodomethane ($CF_3I$).

The azeotrope or azeotrope-like composition comprises, consists essentially of, or consists of, from about 24 wt. % to about 54 wt. % 1,1,3,3,3-pentafluoropropene (HFO-1225zc), from about 30 wt. % to about 48 wt. % 1,1,3,3,3-pentafluoropropene (HFO-1225zc), from about 38 wt. % to about 39 wt. % 1,1,3,3,3-pentafluoropropene (HFO-1225zc), or about 38.99 wt. % 1,1,3,3,3-pentafluoropropene (HFO-1225zc), and from about 46 wt. % to about 76 wt. % trifluoroiodomethane ($CF_3I$), from about 52 wt. % to about 70 wt. % trifluoroiodomethane ($CF_3I$), from about 61 wt. % to about 62 wt. % trifluoroiodomethane ($CF_3I$), or about 61.01 wt. % trifluoroiodomethane ($CF_3I$).

In other words, the azeotrope or azeotrope-like composition may comprise from about 24 wt. % to about 54 wt. % 1,1,3,3,3-pentafluoropropene (HFO-1225zc) and from about 46 wt. % to about 76 wt. % trifluoroiodomethane ($CF_3I$), from about 30 wt. % to about 48 wt. % 1,1,3,3,3-pentafluoropropene (HFO-1225zc) and from about 52 wt. % to about 70 wt. % trifluoroiodomethane ($CF_3I$), or from about 38 wt. % to about 39 wt. % 1,1,3,3,3-pentafluoropropene (HFO-1225zc) and from about 61 wt. % to about 62 wt. % trifluoroiodomethane ($CF_3I$), or about 38.99 wt. % 1,1,3,3,3-pentafluoropropene (HFO-1225zc) and about 61.01 wt. % trifluoroiodomethane ($CF_3I$). The azeotrope of azeotrope-like composition may consist essentially of 1,1,3,3,3-pentafluoropropene (HFO-1225zc) and trifluoroiodomethane ($CF_3I$) in the above amounts, or consist of 1,1,3,3,3-pentafluoropropene (HFO-1225zc) and trifluoroiodomethane ($CF_3I$) in the above amounts.

The azeotrope or azeotrope-like composition has a boiling point of about −25.63° C.±0.30° C. at a pressure of about 14.44 psia±0.30 psia.

In another form thereof, the present disclosure provides an azeotrope or azeotrope-like composition consisting essentially of 1,1,3,3,3-pentafluoropropene (HFO-1225zc) and trifluoroiodomethane ($CF_3I$) has a boiling point of about −25.63° C.±0.30° C. at a pressure of about 14.44 psia±0.30 psia.

In a further form thereof, the present disclosure provides a method of forming an azeotrope or azeotrope-like composition comprising the step of combining 1,1,3,3,3-pentafluoropropene (HFO-1225zc) and trifluoroiodomethane ($CF_3I$) to form an azeotrope or azeotrope-like composition comprising, consisting essentially of, or consisting of 1,1,3,3,3-pentafluoropropene (HFO-1225zc) and trifluoroiodomethane ($CF_3I$). The azeotrope or azeotrope-like composition may have a boiling point of about −25.63° C.±0.30° C. at a pressure of about 14.44 psia±0.30 psia.

In a still further form thereof, the present disclosure provides a method of separating 1,1,3,3,3-pentafluoropropene (HFO-1225zc) and trifluoroiodomethane ($CF_3I$) from a primary composition comprising 1,1,3,3,3-pentafluoropropene (HFO-1225zc), trifluoroiodomethane ($CF_3I$), and at least one impurity, including the steps of: forming, within the primary composition, a secondary composition which is an azeotrope or azeotrope-like composition comprising, consisting essentially of, or consisting of effective amounts of 1,1,3,3,3-pentafluoropropene (HFO-1225zc) and trifluoroiodomethane ($CF_3I$) where the azeotrope or azeotrope-like composition may have a boiling point of about −25.63° C.±0.30° C. at a pressure of about 14.44 psia±0.30 psia; and separating the secondary composition from the primary composition and the at least one impurity.

In the foregoing method, the forming step may comprise forming, within the primary composition, a secondary composition which is an azeotrope or azeotrope-like composition comprising, consisting essentially of, or consisting of from about 24 wt. % to about 54 wt. % 1,1,3,3,3-pentafluoropropene (HFO-1225zc) and from about 46 wt. % to about 76 wt. % trifluoroiodomethane ($CF_3I$) and having a boiling point of about −25.63° C.±0.30° C. at a pressure of about 14.44 psia±0.30 psia.

DESCRIPTION OF THE DRAWINGS

The FIGURE is a plot of temperature vs. weight percent 1,1,3,3,3-pentafluoropropene (HFO-1225zc) measured according to Example 1.

DETAILED DESCRIPTION

It has been found that 1,1,3,3,3-pentafluoropropene (HFO-1225zc) forms homogeneous, minimum boiling azeotrope and azeotrope-like compositions or mixtures with trifluoroiodomethane ($CF_3I$), and the present disclosure provides homogeneous azeotrope or azeotrope-like compositions comprising 1,1,3,3,3-pentafluoropropene (HFO-1225zc) and trifluoroiodomethane ($CF_3I$). The azeotrope or azeotrope-like compositions may consist essentially of 1,1,3,3,3-pentafluoropropene (HFO-1225zc) and trifluoroiodomethane ($CF_3I$), or the azeotrope or azeotrope-like compositions may consist of 1,1,3,3,3-pentafluoropropene (HFO-1225zc) and trifluoroiodomethane ($CF_3I$).

The present inventors have found experimentally that 1,1,3,3,3-pentafluoropropene (HFO-1225zc) and trifluoroiodomethane ($CF_3I$) form an azeotrope or azeotrope-like composition.

An "azeotrope" composition is a unique combination of two or more components. An azeotrope composition can be characterized in various ways. For example, at a given pressure, an azeotrope composition boils at a constant characteristic temperature which is either greater than the higher boiling point component (maximum boiling azeotrope) or less than the lower boiling point component (minimum boiling azeotrope). At this characteristic temperature the same composition will exist in both the vapor and liquid phases. The azeotrope composition does not fractionate upon boiling or evaporation. Therefore, the components of the azeotrope composition cannot be separated during a phase change.

An azeotrope composition is also characterized in that at the characteristic azeotrope temperature, the bubble point pressure of the liquid phase is identical to the dew point pressure of the vapor phase.

The behavior of an azeotrope composition is in contrast with that of a non-azeotrope composition in which during boiling or evaporation, the liquid composition changes to a substantial degree.

For the purposes of the present disclosure, an azeotrope composition is characterized as that composition which boils at a constant characteristic temperature, the temperature being lower (a minimum boiling azeotrope) than the boiling points of the two or more components, and thereby having the same composition in both the vapor and liquid phases.

One of ordinary skill in the art would understand however that at different pressures, both the composition and the boiling point of the azeotrope composition will vary to some extent. Therefore, depending on the temperature and/or pressure, an azeotrope composition can have a variable composition. The skilled person would therefore understand that composition ranges, rather than fixed compositions, can be used to define azeotrope compositions. In addition, an azeotrope may be defined in terms of exact weight percentages of each component of the compositions characterized by a fixed boiling point at a specified pressure.

An "azeotrope-like" composition is a composition of two or more components which behaves substantially as an azeotrope composition. Thus, for the purposes of this disclosure, an azeotrope-like composition is a combination of two or more different components which, when in liquid form under given pressure, will boil at a substantially constant temperature, and which will provide a vapor composition substantially identical to the liquid composition undergoing boiling.

For the purposes of this disclosure, an azeotrope-like composition is a composition or range of compositions which boils at a temperature range of about −25.63° C.±0.30° C. at a pressure of about 14.44 psia±0.30 psia.

Azeotrope or azeotrope-like compositions can be identified using a number of different methods.

For the purposes of this disclosure the azeotrope or azeotrope-like composition is identified experimentally using an ebulliometer (Walas, Phase Equilibria in Chemical Engineering, Butterworth-Heinemann, 1985, 533-544). An ebulliometer is designed to provide extremely accurate measurements of the boiling points of liquids by measuring the temperature of the vapor-liquid equilibrium.

The boiling points of each of the components alone are measured at a constant pressure. As the skilled person will appreciate, for a binary azeotrope or azeotrope-like composition, the boiling point of one of the components of the composition is initially measured. The second component of the composition is then added in varying amounts and the boiling point of each of the obtained compositions is measured using the ebulliometer at said constant pressure.

The measured boiling points are plotted against the composition of the tested composition, for example, for a binary azeotrope, the amount of the second component added to the composition, (expressed as either weight % or mole %). The presence of an azeotrope composition can be identified by the observation of a maximum or minimum boiling temperature which is greater or less than the boiling points of any of the components alone.

As the skilled person will appreciate, the identification of the azeotrope or azeotrope-like composition is made by the comparison of the change in the boiling point of the composition on addition of the second component to the first component, relative to the boiling point of the first component. Thus, it is not necessary that the system be calibrated to the reported boiling point of the particular components in order to measure the change in boiling point.

As previously discussed, at the maximum or minimum boiling point, the composition of the vapor phase will be identical to the composition of the liquid phase. The azeotrope-like composition is therefore that composition of components which provides a substantially constant minimum or maximum boiling point, that is a boiling point of about −25.63° C.±0.30° C. at a pressure of about 14.44 psia±0.30 psia, at which substantially constant boiling point the composition of the vapor phase will be substantially identical to the composition of the liquid phase.

The present disclosure provides an azeotrope or azeotrope-like composition which comprises effective amounts of 1,1,3,3,3-pentafluoropropene (HFO-1225zc) and trifluoroiodomethane ($CF_3I$) to form an azeotrope or azeotrope-like composition. As used herein, the term "effective amount" is an amount of each component which, when combined with the other component, results in the formation of an azeotrope or azeotrope-like mixture.

The present azeotrope or azeotrope-like compositions may consist essentially of combinations of 1,1,3,3,3-pentafluoropropene (HFO-1225zc) and trifluoroiodomethane ($CF_3I$), or consist of combinations of 1,1,3,3,3-pentafluoropropene (HFO-1225zc) and trifluoroiodomethane ($CF_3I$).

As used herein, the term "consisting essentially of", with respect to the components of an azeotrope or azeotrope-like composition or mixture, means the composition contains the indicated components in an azeotrope or azeotrope-like ratio, and may contain additional components provided that the additional components do not form new azeotrope or azeotrope-like systems. For example, azeotrope mixtures consisting essentially of two compounds are those that form binary azeotropes, which optionally may include one or more additional components, provided that the additional components do not render the mixture non-azeotropic and do not form an azeotrope with either or both of the compounds (e.g., do not form a ternary or higher azeotrope).

The present disclosure also provides a method of forming an azeotrope or azeotrope-like composition by mixing, combining, or blending, effective amounts of, 1,1,3,3,3-pentafluoropropene (HFO-1225zc) and trifluoroiodomethane ($CF_3I$). Any of a wide variety of methods known in the art for combining two or more components to form a composition can be used in the present methods. For example, 1,1,3,3,3-pentafluoropropene (HFO-1225zc) and trifluoroiodomethane ($CF_3I$) can be mixed, blended, or otherwise combined by hand and/or by machine, as part of a batch or continuous reaction and/or process, or via combinations of two or more such steps. Both 1,1,3,3,3-pentafluoropropene (HFO-1225zc) and trifluoroiodomethane ($CF_3I$) are commercially available and can be procured from several different vendors. The components can be provided in the required amounts, for example by weighing and then combining the amounts.

The azeotrope or azeotrope-like composition comprises, consists essentially of, or consists of, from about 24 wt. % to about 54 wt. % 1,1,3,3,3-pentafluoropropene (HFO-1225zc), from about 30 wt. % to about 48 wt. % 1,1,3,3,3-pentafluoropropene (HFO-1225zc), from about 38 wt. % to about 39 wt. % 1,1,3,3,3-pentafluoropropene (HFO-1225zc), or about 38.99 wt. % 1,1,3,3,3-pentafluoropropene (HFO-1225zc), and from about 46 wt. % to about 76 wt. % trifluoroiodomethane ($CF_3I$), from about 52 wt. % to about 70 wt. % trifluoroiodomethane ($CF_3I$), from about 61 wt. % to about 62 wt. % trifluoroiodomethane ($CF_3I$), or about 61.01 wt. % trifluoroiodomethane ($CF_3I$). The azeotrope or azeotrope-like composition has a boiling point of about −25.63° C.±0.30° C. at a pressure of about 14.44 psia±0.30 psia.

In other words, the azeotrope or azeotrope-like composition may comprise from about 24 wt. % to about 54 wt. % 1,1,3,3,3-pentafluoropropene (HFO-1225zc) and from about 46 wt. % to about 76 wt. % trifluoroiodomethane ($CF_3I$), from about 30 wt. % to about 48 wt. % 1,1,3,3,3-pentafluoropropene (HFO-1225zc) and from about 52 wt. % to about 70 wt. % trifluoroiodomethane ($CF_3I$), or from about from about 38 wt. % to about 39 wt. % 1,1,3,3,3-pentafluoropropene (HFO-1225zc) and from about 61 wt. % to about 62 wt. % trifluoroiodomethane ($CF_3I$), or about 38.99 wt. % 1,1,3,3,3-pentafluoropropene (HFO-1225zc) and about 61.01 wt. % trifluoroiodomethane ($CF_3I$). The azeotrope or azeotrope-like composition may consist essentially of 1,1,3,3,3-pentafluoropropene (HFO-1225zc) and trifluoroiodomethane ($CF_3I$) in the above amounts, or consist of 1,1,3,3,3-pentafluoropropene (HFO-1225zc) and trifluoroiodomethane ($CF_3I$) in the above amounts.

The azeotrope or azeotrope-like composition of the present disclosure has a boiling point of about −25.63° C.±0.30° C. at a pressure of about 14.44 psia±0.30 psia.

Stated alternatively, the azeotrope or azeotrope-like composition comprises, consists essentially of, or consists of, as little as about 24 wt. %, or about 30 wt. %, or about 38 wt. %, or as great as about 39 wt. %, or about 48 wt. %, or about 54 wt. % 1,1,3,3,3-pentafluoropropene (HFO-1225zc), or within any range defined between any two of the foregoing values, and the azeotrope or azeotrope-like composition comprises, consists essentially of, or consists of, as little as about 46 wt. %, about 52 wt. %, or about 61 wt. %, or as great as about 62 wt. %, about 70 wt. %, or about 76 wt. % trifluoroiodomethane ($CF_3I$), or within any range defined between any two of the foregoing values. In one embodiment, the azeotrope or azeotrope-like composition comprises, consists essentially of, or consists of, about 38.99 wt. % and 1,1,3,3,3-pentafluoropropene (HFO-1225zc) and about 61.01 wt. % of trifluoroiodomethane ($CF_3I$). The azeotrope or azeotrope-like composition of the present disclosure has a boiling point of about −25.63° C.±0.30° C. at a pressure of about 14.44 psia±0.30 psia.

The present disclosure also provides a composition comprising the azeotrope or azeotrope-like compositions. For example, there is provided a composition comprising at least about 5 wt. % of the azeotrope or azeotrope-like composition, or at least about 15 wt. % of the azeotrope or azeotrope-like composition, or at least about 50 wt. % of the azeotrope or azeotrope-like composition, or at least about 70 wt. % of the azeotrope or azeotrope-like composition, or at least about 90 wt. % of the azeotrope or azeotrope-like composition.

The azeotrope or azeotrope-like composition comprising, consisting essentially of, or consisting of effective amounts of 1,1,3,3,3-pentafluoropropene (HFO-1225zc) and trifluoroiodomethane ($CF_3I$) disclosed herein may be used for separating impurities from 1,1,3,3,3-pentafluoropropene (HFO-1225zc) and/or trifluoroiodomethane ($CF_3I$). One impurity that may be present in trifluoroiodomethane ($CF_3I$) is trifluoromethane (HFC-23).

The preparation of azeotropic or azeotrope-like compositions comprising, consisting essentially of, or consisting of effective amounts of 1,1,3,3,3-pentafluoropropene (HFO-1225zc) and trifluoroiodomethane ($CF_3I$) allows separation techniques such as azeotropic distillation, for example, to be used to remove impurities from trifluoroiodomethane ($CF_3I$) to provide trifluoroiodomethane ($CF_3I$) of high purity.

In one example, an azeotrope or azeotrope-like composition comprising, consisting essentially of, or consisting of effective amounts of 1,1,3,3,3-pentafluoropropene (HFO-1225zc) and trifluoroiodomethane ($CF_3I$) may be formed from a composition including one or both of 1,1,3,3,3-pentafluoropropene (HFO-1225zc) and trifluoroiodomethane ($CF_3I$) together with one or more other chemical compounds other than 1,1,3,3,3-pentafluoropropene (HFO-1225zc) and trifluoroiodomethane ($CF_3I$), such as impurities. Following the formation of the azeotrope or azeotrope-like composition, the azeotrope or azeotrope-like composition may be separated from the other chemical compounds by a suitable method, such as by distillation, phase separation, or fractionation.

In this manner, the present disclosure provides a method of separating 1,1,3,3,3-pentafluoropropene (HFO-1225zc) and/or trifluoroiodomethane ($CF_3I$) from at least one impurity, including the steps of providing a primary composition including 1,1,3,3,3-pentafluoropropene (HFO-1225zc), trifluoroiodomethane ($CF_3I$) and at least one impurity to form a secondary composition which is an azeotrope or azeotrope-like composition comprising, consisting essentially of, or consisting of effective amounts of 1,1,3,3,3-pentafluoropropene (HFO-1225zc) and trifluoroiodomethane ($CF_3I$), and may have a boiling point of about −25.63° C.±0.30° C. at a pressure of about 14.44 psia±0.30 psia within the primary composition, and separating secondary composition from primary composition by a separation technique such as phase separation, distillation, or fractionation, for example.

In this manner, the present disclosure provides a method of separating 1,1,3,3,3-pentafluoropropene (HFO-1225zc) as an impurity from a primary, crude composition of trifluoroiodomethane ($CF_3I$) which includes 1,1,3,3,3-pentafluoropropene (HFO-1225zc) as an impurity together with at least one additional impurity, including the steps of providing a primary composition of crude trifluoroiodomethane ($CF_3I$), 1,1,3,3,3-pentafluoropropene (HFO-1225zc) as an impurity, and at least one additional impurity, and subjecting the primary composition to distillation, for example, at conditions effective to form a secondary composition which is an azeotrope or azeotrope-like composition comprising, consisting essentially of, or consisting of effective amounts of 1,1,3,3,3-pentafluoropropene (HFO-1225zc) and trifluoroiodomethane ($CF_3I$), and separating the secondary composition from the primary composition by a separation technique such as phase separation, distillation, or fractionation, for example. Thereafter, the primary composition may be subjected to further separation or purification steps to obtain purified trifluoroiodomethane ($CF_3I$).

The following non-limiting Examples serve to illustrate the disclosure.

EXAMPLES

Example 1—Ebulliometer Study

An ebulliometer was used to measure azeotrope and azeotrope-like compositions of 1,1,3,3,3-pentafluoropropene (HFO-1225zc) and trifluoroiodomethane ($CF_3I$). The ebulliometer included a vacuum jacketed glass vessel which was sealed at the bottom and open to the atmosphere at the top. The top, or condenser jacket, of the ebulliometer was filled with a mixture of dry ice and ethanol to attain a temperature of about −72° C., which is significantly lower than the normal boiling points of −22.12° C. for 1,1,3,3,3-pentafluoropropene (HFO-1225zc) and −22.1520° C. for trifluoroiodomethane ($CF_3I$) at a pressure of 14.44 psia. In this manner, it was ensured that all vapors in the system were condensed and flowed back into the ebulliometer such that the liquid and vapor phases were in equilibrium. A quartz-platinum thermometer with an accuracy of +0.002° C. was inserted inside the glass vessel and used to determine the temperature of the condensed vapor corresponding to the equilibrium boiling point of the mixture. Boiling chips were used to assist with maintaining a smooth boiling of the mixture in the ebulliometer.

The following procedure was used.

1. The quartz thermometer was immersed into a long dewar which contained an ice/water slurry and it was verified that the thermometer read 0° C. The dewar was deep enough so that at least the length of the thermometer shaft was immersed in the ice/water. The thermometer resistance was recorded in ohms.

2. The condenser jacket was loaded to ¼ full with ethanol. The condenser jacket was cooled by slowly introducing dry ice to avoid boiling over and/or splashing of the ethanol.

3. A known amount of trifluoroiodomethane ($CF_3I$) or 1,1,3,3,3-pentafluoropropene (HFO-1225zc) was added to the ebulliometer and brought to a vigorously refluxing condition. The temperature and atmospheric pressure were recorded using a barometer with a temperature indicator.

The measurement was carried out in two steps. In a first step, about 24.30 g of trifluoroiodomethane ($CF_3I$) having a purity of 99.88 area % as determined by gas chromatography (GC) was first introduced to the ebulliometer by weighing the container before and after the addition using a balance having an accuracy of ±0.01 g. The liquid was brought to a boil and the equilibrium temperature of the trifluoroiodomethane ($CF_3I$) was recorded at the recorded barometric pressure. Then, 1,1,3,3,3-pentafluoropropene (HFO-1225zc) having a purity of 99.8 area % as determined by gas chromatography (GC) was introduced in small increments into the ebulliometer and the equilibrium temperature of the condensed liquid mixture was recorded.

In a second step, about 14.04 g of 1,1,3,3,3-pentafluoropropene (HFO-1225zc) having a purity of 99.99 area % as determined by gas chromatography (GC) was introduced to the ebulliometer by weighing the container before and after the addition using a balance having an accuracy of ±0.01 g. The liquid was brought to a boil and the equilibrium temperature of the 1,1,3,3,3-pentafluoropropene (HFO-1225zc) was recorded at the recorded barometric pressure. Then, trifluoroiodomethane ($CF_3I$) having a purity of 99.88 area % as determined by gas chromatography (GC) was introduced in small increments into the ebulliometer and the equilibrium temperature of the condensed liquid mixture was recorded.

Data from the above first and second steps was combined to complete the composition range data from 0 to 100 weight percent of each of the 1,1,3,3,3-pentafluoropropene (HFO-1225zc) and the trifluoroiodomethane ($CF_3I$) presented below in Table 1, which shows a minimum in temperature which indicates that an azeotrope had been formed, and this data is also presented in graphic form in FIG. 1. The bubble point temperature of the mixture remained constant indicating that the mixture was azeotrope-like over a large composition range.

TABLE 1

Ebulliometer Study of $CF_3I$/HF) 1225zc at P = 14.44 psia

| T (° C.) (+/−0.01° C.) | wt. % HFO-1225zc (+/−0.1) | wt. % $CF_3I$ (+/−0.1) |
|---|---|---|
| −22.12 | 100.00 | 0.00 |
| −22.69 | 97.77 | 2.23 |
| −23.01 | 94.29 | 5.71 |
| −23.44 | 90.23 | 9.77 |
| −23.70 | 87.53 | 12.47 |
| −24.06 | 83.13 | 16.87 |
| −24.46 | 76.89 | 23.11 |
| −24.74 | 71.82 | 28.18 |
| −25.04 | 65.24 | 34.76 |
| −25.17 | 61.69 | 38.31 |
| −25.31 | 58.26 | 41.74 |
| −25.41 | 54.17 | 45.83 |
| −25.45 | 51.50 | 48.50 |
| −25.51 | 49.35 | 50.65 |
| −25.54 | 46.18 | 53.82 |

TABLE 1-continued

| Ebulliometer Study of $CF_3I$/HF) 1225zc at P = 14.44 psia | | |
|---|---|---|
| T (° C.) (+/−0.01° C.) | wt. % HFO-1225zc (+/−0.1) | wt. % $CF_3I$ (+/−0.1) |
| −25.56 | 46.42 | 53.58 |
| −25.62 | 42.89 | 57.11 |
| −25.63 | 38.99 | 61.01 |
| −25.61 | 33.51 | 66.49 |
| −25.50 | 28.70 | 71.30 |
| −25.40 | 24.27 | 75.73 |
| −25.26 | 20.56 | 79.44 |
| −24.79 | 12.60 | 87.40 |
| −23.56 | 4.30 | 95.70 |
| −22.51 | 0.82 | 99.18 |
| −22.15 | 0.00 | 100.00 |

Example 2—Separation of Impurities

In this Example, a crude composition of trifluoroiodomethane ($CF_3I$) is provided, including 1,1,3,3,3-pentafluoropropene (HFO-1225zc) as an impurity, along with other impurities such as trifluoromethane (HFC-23). This composition is then subjected to distillation at conditions effective to form and separate an azeotrope or azeotrope-like composition of 1,1,3,3,3-pentafluoropropene (HFO-1225zc) and trifluoroiodomethane ($CF_3I$) from the remainder of the composition. The separated azeotrope or azeotrope-like composition of 1,1,3,3,3-pentafluoropropene (HFO-1225zc) and trifluoroiodomethane ($CF_3I$) is removed from the remaining crude composition of trifluoroiodomethane ($CF_3I$) as a light component. The remaining crude composition of trifluoroiodomethane ($CF_3I$) is then subjected to different temperature and pressure conditions wherein the other impurities such as trifluoromethane (HFC-23) may be separated by further distillation to obtain purified trifluoroiodomethane ($CF_3I$).

ASPECTS

Aspect 1 is an azeotrope or azeotrope-like composition comprising effective amounts of 1,1,3,3,3-pentafluoropropene (HFO-1225zc) and trifluoroiodomethane ($CF_3I$).

Aspect 2 is the azeotrope or azeotrope-like composition of Aspect 1, comprising from about 24 wt. % to about 54 wt. % 1,1,3,3,3-pentafluoropropene (HFO-1225zc) and from about 46 wt. % to about 76 wt. % trifluoroiodomethane ($CF_3I$).

Aspect 3 is the azeotrope or azeotrope-like composition of Aspect 2, comprising from about 30 wt. % to about 48 wt. % 1,1,3,3,3-pentafluoropropene (HFO-1225zc) and from about 52 wt. % to about 70 wt. % trifluoroiodomethane ($CF_3I$).

Aspect 4 is the azeotrope or azeotrope-like composition of Aspect 3, comprising from about 38 wt. % to about 39 wt. % 1,1,3,3,3-pentafluoropropene (HFO-1225zc) and from about 61 wt. % to about 62 wt. % trifluoroiodomethane ($CF_3I$).

Aspect 5 is the azeotrope or azeotrope-like composition of Aspect 4, comprising about 38.99 wt. % 1,1,3,3,3-pentafluoropropene (HFO-1225zc) and about 61.01 wt. % trifluoroiodomethane ($CF_3I$).

Aspect 6 is the azeotrope or azeotrope-like composition of any of Aspects 1 to 5, wherein the composition has a boiling point of about −25.63° C.±0.30° C. at a pressure of about 14.44 psia±0.30 psia.

Aspect 7 is the azeotrope or azeotrope-like composition of any of Aspects 1 to 6, consisting essentially of 1,1,3,3,3-pentafluoropropene (HFO-1225zc) and trifluoroiodomethane ($CF_3I$).

Aspect 8 is the azeotrope or azeotrope-like composition of any of Aspects 1 to 7, consisting of 1,1,3,3,3-pentafluoropropene (HFO-1225zc) and trifluoroiodomethane ($CF_3I$).

Aspect 9 is a composition comprising the azeotrope or azeotrope-like composition of any of Aspects 1 to 8.

Aspect 10 is the composition of Aspect 9, comprising at least about 5 wt. % of the azeotrope or azeotrope-like composition.

Aspect 11 is the composition of Aspect 10, comprising at least about 15 wt. % of the azeotrope or azeotrope-like composition.

Aspect 12 is the composition of Aspect 11, comprising at least about 50 wt. % of the azeotrope or azeotrope-like composition.

Aspect 13 is the composition of Aspect 12, comprising at least about 70 wt. % of the azeotrope or azeotrope-like composition.

Aspect 14 is the composition of Aspect 13, comprising at least about 90 wt. % of the azeotrope or azeotrope-like composition.

Aspect 15 is a method of forming an azeotrope or azeotrope-like composition comprising the step of combining 1,1,3,3,3-pentafluoropropene (HFO-1225zc) and trifluoroiodomethane ($CF_3I$) to form the azeotrope or azeotrope-like composition comprising effective amounts of 1,1,3,3,3-pentafluoropropene (HFO-1225zc) and trifluoroiodomethane ($CF_3I$).

Aspect 16 is the method of Aspect 15, the method comprising the step of combining 1,1,3,3,3-pentafluoropropene (HFO-1225zc) and trifluoroiodomethane ($CF_3I$) to form the azeotrope or azeotrope-like composition of any of Aspects 1 to 7.

Aspect 17 is a method of separating 1,1,3,3,3-pentafluoropropene (HFO-1225zc) and trifluoroiodomethane ($CF_3I$) from a primary composition comprising 1,1,3,3,3-pentafluoropropene (HFO-1225zc), trifluoroiodomethane ($CF_3I$) and at least one impurity, including the steps of forming, within the primary composition, a secondary composition which is an azeotrope or azeotrope-like composition comprising effective amounts of 1,1,3,3,3-pentafluoropropene (HFO-1225zc) and trifluoroiodomethane ($CF_3I$); and separating the secondary composition from the primary composition and the at least one impurity.

Aspect 18 is the method of Aspect 17, wherein the azeotrope or azeotrope-like composition is as defined in any of Aspects 1 to 8.

Aspect 19 is the method of Aspect 17 or 18, in which the separation is carried out by at least one of phase separation, distillation, and fractionation.

As used herein, the phrase "within any range defined between any two of the foregoing values" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the disclosure be limited to the specific values recited when defining a range.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances that fall within the scope of the appended claims.

What is claimed is:

1. A composition comprising an azeotrope or azeotrope-like composition consisting essentially of effective amounts of 1,1,3,3,3-pentafluoropropene (HFO-1225zc) and trifluoroiodomethane ($CF_3I$).

2. The composition of claim 1, wherein the azeotrope or azeotrope-like composition has a boiling point of about −25.63° C.±0.30° C. at a pressure of about 14.44 psia±0.30 psia.

3. The composition of claim 1, wherein the azeotrope or azeotrope-like composition consists essentially of from about 24 wt. % to about 54 wt. % 1,1,3,3,3-pentafluoropropene (HFO-1225zc) and from about 46 wt. % to about 76 wt. % trifluoroiodomethane ($CF_3I$).

4. The composition of claim 1, wherein the azeotrope or azeotrope-like composition consists essentially of from about 30 wt. % to about 48 wt. % 1,1,3,3,3-pentafluoropropene (HFO-1225zc) and from about 52 wt. % to about 70 wt. % trifluoroiodomethane ($CF_3I$).

5. The composition of claim 1, wherein the azeotrope or azeotrope-like composition comprises from about 38 wt. % to about 39 wt. % 1,1,3,3,3-pentafluoropropene (HFO-1225zc) and from about 61 wt. % to about 62 wt. % trifluoroiodomethane ($CF_3I$).

6. The composition of claim 1, wherein the azeotrope or azeotrope-like composition comprises about 38.99 wt. % 1,1,3,3,3-pentafluoropropene (HFO-1225zc) and about 60.01 wt. % trifluoroiodomethane ($CF_3I$).

7. A composition comprising an azeotrope or azeotrope-like composition consisting essentially of 1,1,3,3,3-pentafluoropropene (HFO-1225zc) and trifluoroiodomethane ($CF_3I$) having a boiling point of about −25.63° C.±0.30° C. at a pressure of about 14.44 psia±0.30 psia.

8. The composition of claim 7, wherein the azeotrope or azeotrope-like composition consists essentially of from about 24 wt. % to about 54 wt. % 1,1,3,3,3-pentafluoropropene (HFO-1225zc) and from about 46 wt. % to about 76 wt. % trifluoroiodomethane ($CF_3I$).

9. The composition of claim 7, wherein the azeotrope or azeotrope-like composition consists essentially of from about 30 wt. % to about 48 wt. % 1,1,3,3,3-pentafluoropropene (HFO-1225zc) and from about 52 wt. % to about 70 wt. % trifluoroiodomethane ($CF_3I$).

10. The composition of claim 7, wherein the azeotrope or azeotrope-like composition consists essentially of from about 38 wt. % to about 39 wt. % 1,1,3,3,3-pentafluoropropene (HFO-1225zc) and from about 61 wt. % to about 62 wt. % trifluoroiodomethane ($CF_3I$).

11. The composition of claim 7, wherein the azeotrope or azeotrope-like composition consists essentially of about 38.99 wt. % 1,1,3,3,3-pentafluoropropene (HFO-1225zc) and about 60.01 wt. % trifluoroiodomethane ($CF_3I$).

12. The composition of claim 7, wherein the azeotrope or azeotrope-like composition consists of from about 24 wt. % to about 54 wt. % 1,1,3,3,3-pentafluoropropene (HFO-1225zc) and from about 46 wt. % to about 76 wt. % trifluoroiodomethane ($CF_3I$).

13. The composition of claim 7, wherein the azeotrope or azeotrope-like composition consists of from about 30 wt. % to about 48 wt. % 1,1,3,3,3-pentafluoropropene (HFO-1225zc) and from about 52 wt. % to about 70 wt. % trifluoroiodomethane ($CF_3I$).

14. The composition of claim 7, wherein the azeotrope or azeotrope-like composition consists of about 38.99 wt. % 1,1,3,3,3-pentafluoropropene (HFO-1225zc) and about 60.01 wt. % trifluoroiodomethane ($CF_3I$).

15. A method of forming an azeotrope or azeotrope-like composition comprising the step of combining 1,1,3,3,3-pentafluoropropene (HFO-1225zc) and trifluoroiodomethane ($CF_3I$) to form an azeotrope or azeotrope-like composition consisting essentially of 1,1,3,3,3-pentafluoropropene (HFO-1225zc) and trifluoroiodomethane ($CF_3I$) having a boiling point of about −25.63° C.±0.30° C. at a pressure of about 14.44 psia±0.30 psia.

16. The method of claim 15, wherein the combining step comprises combining from about 24 wt. % to about 54 wt. % 1,1,3,3,3-pentafluoropropene (HFO-1225zc) and from about 46 wt. % to about 76 wt. % trifluoroiodomethane ($CF_3I$).

17. The method of claim 15, wherein the combining step comprises combining from about 38 wt. % to about 39 wt. % 1,1,3,3,3-pentafluoropropene (HFO-1225zc) and from about 61 wt. % to about 62 wt. % trifluoroiodomethane ($CF_3I$).

18. The method of claim 15, wherein the combining step comprises combining about 38.99 wt. % 1,1,3,3,3-pentafluoropropene (HFO-1225zc) and about 60.01 wt. % trifluoroiodomethane ($CF_3I$).

19. A method of separating 1,1,3,3,3-pentafluoropropene (HFO-1225zc) and trifluoroiodomethane ($CF_3I$) from a primary composition comprising 1,1,3,3,3-pentafluoropropene (HFO-1225zc), trifluoroiodomethane ($CF_3I$) and at least one impurity, including the steps of:

forming, within the primary composition, a secondary composition which is an azeotrope or azeotrope-like composition consisting essentially of effective amounts of 1,1,3,3,3-pentafluoropropene (HFO-1225zc) and trifluoroiodomethane ($CF_3I$) having a boiling point of −25.63° C.±0.30° C. at a pressure of about 14.44 psia±0.30 psia; and separating the secondary composition from the primary composition at least one impurity.

20. The method of claim 19, wherein the forming step comprises forming, within the primary composition, a secondary composition which is an azeotrope or azeotrope-like composition consisting essentially of from about 24 wt. % to about 54 wt. % 1,1,3,3,3-pentafluoropropene (HFO-1225zc) and from about 46 wt. % to about 76 wt. % trifluoroiodomethane ($CF_3I$) and having a boiling point of −25.63° C.±0.30° C. at a pressure of about 14.44 psia±0.30 psia.

* * * * *